United States Patent [19]

Coburn

[11] Patent Number: 4,784,650
[45] Date of Patent: Nov. 15, 1988

[54] NEEDLE HOLDER

[76] Inventor: Timothy J. Coburn, 4 Eliot Cir., Acton, Mass. 01720

[21] Appl. No.: 28,789

[22] Filed: Mar. 23, 1987

[51] Int. Cl.⁴ .............................................. A61M 5/32
[52] U.S. Cl. .................................... 604/272; 128/764; 128/763; 604/317
[58] Field of Search ............... 604/110, 263, 192, 198, 604/197, 905, 411, 414, 408, 409, 410, 322, 283, 86, 257, 317, 403; 128/763, 764; 206/806

[56] References Cited

U.S. PATENT DOCUMENTS

| | | | |
|---|---|---|---|
| 1,465,720 | 8/1923 | Petroff | 604/317 |
| 1,647,210 | 11/1927 | Bryans | 604/403 |
| 2,727,517 | 12/1955 | Wilkin | 128/763 |
| 3,382,865 | 5/1968 | Worrall, Jr. | 128/764 |
| 3,518,164 | 6/1970 | Andelin et al. | 128/763 |
| 3,520,292 | 11/1966 | Barr | 604/197 |
| 3,536,061 | 10/1970 | Ogle | 128/764 |
| 3,687,296 | 8/1972 | Spinosa et al. | 128/764 |
| 3,734,080 | 5/1973 | Petterson et al. | 128/764 |
| 3,741,217 | 6/1973 | Chiarico | 604/283 |
| 3,851,790 | 12/1974 | Kasper | 206/806 |
| 4,046,276 | 9/1977 | Winchell et al. | 604/257 |
| 4,132,225 | 1/1979 | Whattam | 128/763 |
| 4,210,156 | 7/1980 | Bennett | 128/763 |
| 4,215,700 | 8/1980 | Crouther et al. | 128/763 |
| 4,235,350 | 11/1980 | Valentino | 206/806 |
| 4,250,880 | 2/1981 | Gordon | 128/D26 |
| 4,256,120 | 3/1981 | Finley | 128/763 |
| 4,278,437 | 7/1981 | Haggar | 128/764 |
| 4,312,352 | 1/1982 | Meisch et al. | 604/322 |
| 4,312,362 | 1/1982 | Kaufman | 128/763 |
| 4,341,212 | 7/1982 | Medwid | 604/317 |
| 4,392,499 | 7/1983 | Towse | 128/764 |
| 4,412,548 | 11/1983 | Hoch | 128/764 |
| 4,440,161 | 4/1984 | Wadhwa | 128/207.18 |
| 4,576,211 | 3/1986 | Valentini et al. | 604/411 |
| 4,620,549 | 11/1986 | Nugent | 128/763 |
| 4,645,073 | 2/1987 | Homan | 604/414 |
| 4,650,478 | 3/1987 | Dunn | 604/322 |

FOREIGN PATENT DOCUMENTS

| | | | |
|---|---|---|---|
| 1105959 | 7/1981 | Canada | 604/905 |
| 0125944 | 8/1949 | Sweden | 604/414 |

Primary Examiner—Stephen C. Pellegrino
Assistant Examiner—Colleen Reilly
Attorney, Agent, or Firm—Laubscher & Laubscher

[57] ABSTRACT

A holder is disclosed for use with a needle for collecting blood from a donor, the needle having a sharp tip at one end and being mounted in a hub at the other end. The holder is in the form of an elongated tubular member made of plastic and which is open at one end to allow insertion of a blood collection tube and has an opening at the other end to allow insertion of the needle, the latter end being sized so as to allow the needle to pass through but to frictionally engage and snugly hold the hub of the needle when the needle is inserted therein. A cover is hingedly mounted on the holder for closing off the end for receiving the blood collection tube and a bracket is fixedly attached to the tubular member for mounting purposes. The holder may be used as a device for assisting a person in safely and easily inserting the type of needle described above into a blood collection tube and may also be used as a receptacle for temporary or permanent storage of such a needle.

6 Claims, 3 Drawing Sheets

NEEDLE HOLDER

BACKGROUND OF THE INVENTION

The present invention relates generally to a needle holder and more particularly to a needle holder for a hollow type needle having a sharp tip at one end and being mounted in a hub at the other end. Needles of this type are commonly used in collecting blood from a donor.

In a number of medical procedures it is often necessary for a patient to receive a supplementary quantity of blood. Supplies of blood for such a purpose are usually obtained in advance from donors and stored in containers called blood transfusion bags.

Blood transfusion bags are generally fabricated from a plastic material, such as polyvinylchloride, and are sized to hold about 450 milliliters of blood. Each bag has an inlet port through which blood is received from the donor and a pair of outlet ports from which blood is dispensed to a recipient. A length of plastic tubing on the order of about forty-five centimeters or longer extends out from the inlet port and provides a passageway through which blood is transmitted from the donor into the blood transfusion bag.

The length of plastic tubing extending from the inlet port is usually made up of two sections, an inner section and an outer section, with the two sections being interconnected end-to-end to form the overall length of tubing. The inner section is integrally formed with the blood transfusion bag at its inner end and has an elongated hollow rubber fitting, usually circular in external cross-section, at its outer end. The outer section has a hollow straight needle mounted at each end. Each one of the two needles has a sharp tip at its outer end and an elongated rubber hub, usually rectangular in external cross section, at its inner end. The needle at the outer end of the outer section is often referred to as the primary needle and is the needle that is actually inserted into the donor to extract the blood. The needle at the inner end of the outer section is somewhat shorter in length than the primary needle and is usually referred to as the in-line needle. This latter needle is used for a purpose that will hereinafter be explained. The in-line needle is removably mounted in the hollow rubber fitting at the outer end of the inner section.

In addition to filling the blood transfusion bag, it is common practice to also fill about two or three blood collection tubes, called pilot tubes, with blood from the donor for general test purposes (i.e. to determine blood type, etc). These pilot tubes are hollow, evacuated, open at one end and provided with a rubber stopper at the open end to seal the tube and maintain the vacuum within the tube. After the pilot tubes have been filled with blood, the inner section of plastic tubing with blood in it from the donor is usually sealed off at about one and one-half inch increments over its length so as to form a series or chain of about a dozen segments, with each segment having about two milliliters of the same blood that is in the blood transfusion bag. The outer section of tubing and the outer end of the inner section are then removed and discarded. The individual segments so formed are used as needed when the occasion arises for testing with a sample of blood from a recipient to insure that the blood from the donor in the blood transfusion bag will not precipitate some form of reaction in the recipient.

In the past, the pilot tubes have been filled with blood from the donor by either one of two techniques.

One technique involves getting the blood directly from the donor after the blood transfusion bag has been filled. With the primary needle still inserted in the donor the length of plastic tubing extending from the blood transfusion bag is clamped in either side of the in-line needle. In in-line needle is then detached from the hollow rubber fitting. The tip of the in-line needle is then pushed through the rubber stopper in the particular pilot tube which is to be filled with blood and into the interior of the tube. The clamp between the primary needle and the in-line needle is then released allowing blood to flow directly from the donor in the pilot tube. The other pilot tubes are filled the same way, temporarily clamping the tubing while the needle is being transferred from one pilot tube to the next. One of the problems with this technique is that pushing the tip of the needle through the rubber stopper in the pilot tube and into the interior of the pilot tube is by no means an easy task and, on occassion, the person attempting to insert the needle into the tube will end up actually sticking the tip of the needle into his or her finger. Another shortcoming of this technique is that the primary needle is not removed from the donor as soon as the blood transfusion bag is filled with blood but rather stays inserted in the donor while the pilot tubes are being filled. From the donor's standpoint this procedure is not entirely desirable since the donor would prefer to have the needle removed as soon as possible (i.e. once the blood transfusion bag is filled).

The other technique for filling the pilot tubes involves taking the blood from the blood transfusion bag rather than from the donor. In accordance with this other technique, the blood transfusion bag is filled with more than the normal amount of blood it should hold, the amount of additional blood being sufficient to fill two or three pilot tubes. The length of plastic tubing is then clamped near the primary needle. The primary needle is then removed from the donor and inserted through the rubber stopper in the particular pilot tube to be filled with blood. The clamp is then released and the pilot tube filled with blood from the blood transfusion bag. After one pilot tube is filled, the needle is inserted into another pilot tube and so forth. After all of the pilot tubes are filled, the donor is attended to (i.e. gauze or a bandage is placed on the puncture in the skin etc.). Although this second technique involves removing the primary needle from the donor at an earlier point in time than the first technique, it still presents the problem of the technician or nurse being stuck by the needle as it is being inserted into the stopper; and, in fact, in this instance it is a somewhat larger needle (i.e. the primary needle rather than the in-line needle) that is being inserted into the pilot tube. Another problem with this technique is that the donor is not attended to by the technician or nurse until after all of the pilot tubes have been filled. From the donor's viewpoint this is very undesirable. It has been suggested that the donor be attended to before the needle is inserted and pushed through the stopper of the pilot tube. The shortcoming with this suggestion is that there is no place to temporarily store the needle while the donor is being attended to and it is very difficult, if at all possible, to hold the needle and at the same time attend to the donor.

BRIEF DESCRIPTION OF THE PRIOR ART

Needle holders for use with double tipped blood collection needles (i.e. hollow needles having a sharp tip at each end and a hub between the ends that is circular in external cross section and externally threaded over a part of its length) are well known in the art. Double tipped blood collection needles are used normally in collecting blood from a patient, as opposed to collecting blood from a donor. The holders for these needles are used to hold the needle so that one end can be inserted into a patient and the other end inserted into a pilot tube and generally comprise an elongated tubular member made of plastic. One end of the tubular member is open. The other end includes a neck portion having a circular opening that is internally threaded and sized to engage the threaded portion of the hub. In use, the hub of the needle is screwed into the neck portion of the holder. The tip of the needle extending out of the holder is then inserted into the patient and a pilot tube is inserted into the holder, the stoppered end first, and pushed into the tip of the needle extending into the holder until the tip penetrates through the stopper.

It is an object of this invention to provide a new and improved needle holder.

It is another object of this invention to provide a needle holder for use with hollow blood collection needles having a sharp tip at one end and being mounted in a hub rectangular in cross section at the other end.

It is still another object of this invention to provide a needle holder for use in assisting a person in inserting a single tipped blood collection needle through a rubber stopper at the open end of a pilot tube.

It is yet still another object of this invention to provide a needle holder as described above which may also be used as a receptacle for temporary and/or permanent storage for the needle.

It is a further object of this invention to provide a needle holder as described above which can be mounted on a hook or other similar device.

It is still a further object of this invention to provide a needle holder which may be used with either the primary needle or the in-line needle in an apparatus for collecting blood from a donor.

It is yet still another object of this invention to provide a needle holder as described above which can be mass produced and which is disposable.

SUMMARY OF THE INVENTION

A needle holder constructed according to the teachings of the present invention for use with a hollow needle of the type having a sharp tip at one end and a hub mounted at the other end and used in an apparatus for collecting blood from a donor comprises an elongated tubular member whose internal cross-sectional size over its entire length is larger than that of a pilot tube. The tubular member is open at one end so that a pilot tube may be inserted therein and has an opening at the other end which is sized and shaped to frictionally engage and snugly hold the hub of the needle when the needle is inserted therein. A cover is hingedly attached to the holder for closing off the open end, (i.e. the end through which the pilot tube is inserted) when desired, and a bracket is fixedly attached to the holder for mounting the holder onto a hook or other similar device. The tubular member along with the cover and bracket comprise a unitary structure and made of plastic.

The holder may be used as a receptacle for temporary or permanent storage of the needle or as a device to assist a person in safely and easily inserting the tip of the needle through a stopper at the open end of a pilot tube.

In using the holder as a receptacle, the pilot tube receiving end is closed with the cover and the needle inserted through the other end.

In using the holder as a needle insertion assist device, the needle is preferably first inserted into the elongaged tubular member through the needle receiving end, the sharp tip end first, and pushed into the tubular member until the hub frictionally engages the opening. The pilot tube is then inserted into the pilot tube receiving end of the elongated tubular member, the stoppered end first, and moved inward in the tubular member toward the needle until the tip of the needle penetrates through the stopper and into the interior of the pilot tube.

Various features and advantages of the invention will appear from the description to follow. In the description, reference is made to the accompanying drawings which forms a part thereof, and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF PREFERRED EMBODIMENTS

Figure 1:
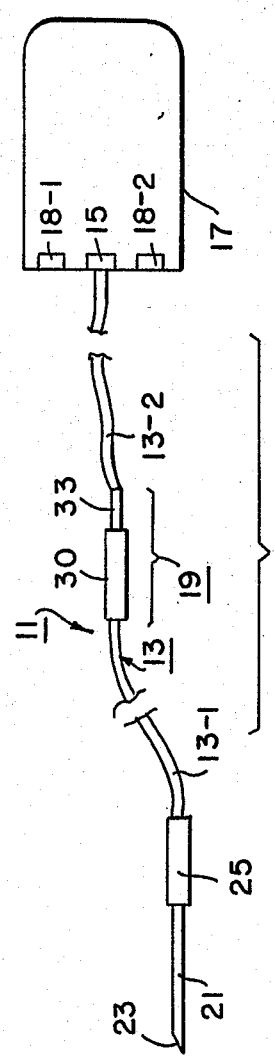
FIG. 1 is a front elevation view of a typical apparatus for collecting blood from a donor.
Figure 2:
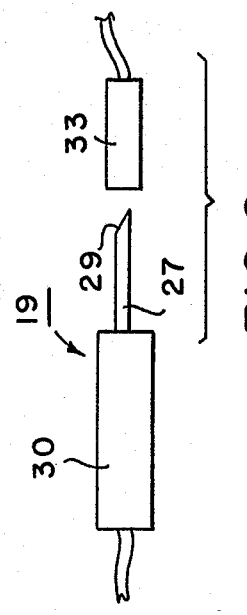
FIG. 2 is an enlarged front elevation view of the in-line needle interface shown in FIG. 1 with the two parts making up the interface being separated from one another.
Figure 5:
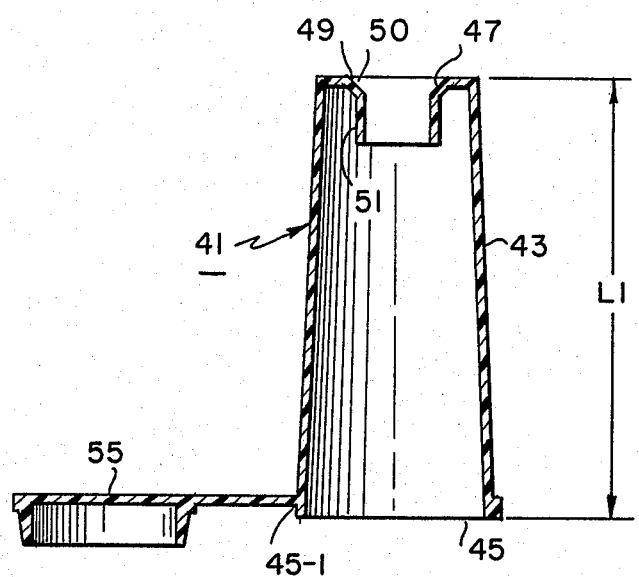
FIG. 5 is a front section view of the device shown in FIG. 4.

Referring now to the drawings and first to FIGS. 1 and 2, there is shown in FIG. 1 a typical apparatus 11 for collecting blood from a donor.

Apparatus 11 includes a length of plastic tubing 13 which extends outward from the inlet port 15 of a blood transfusion bag 17. Blood transfusion bag 17 also includes a pair of outlet ports 18-1 and 18-2. Plastic tubing 13 is made up of an outer tubing section 13-1 and an inner tubing section 13-2, the two sections being connected end-to-end by an interface 19. An elongated hollow needle 21, referred to as a primary needle, is attached to the outer end of outer tubing section 13-1. Primary needle 21 has a sharp tip 23 at its outer end and is mounted on an elongated hub 25 at its inner end. Hub 25 is attached to outer tubing section 13-1. Hub 25 is made of rubber and is rectangular in external cross-section.

Interface 19, which is shown in more detail in FIG. 2, includes an elongated hollow needle 27, referred to as an in-line needle. In-line needle 27 has a sharp tip 29 at its outer end and is mounted on an elongated hub 30 at its inner end which is attached to the inner end of outer tubing section 13-1. In-line needle 27 is removably mounted in a hollow fitting 33 which is attached to inner tubing section 13-2. Fitting 33 is made of rubber and is circular in external cross-section.

Primary needle 21 is usually longer and has a larger sized bore than in-line needle 27.

Figure 3:
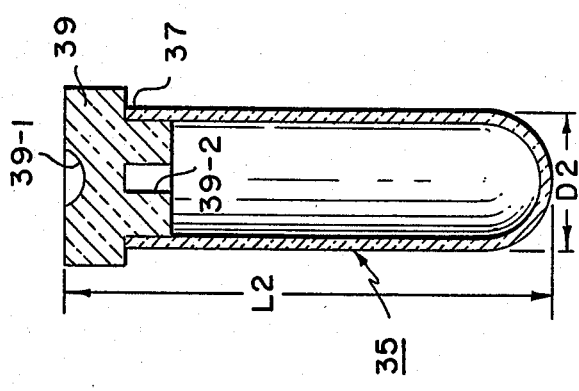
FIG. 3 is a section view of a typical stoppered blood collection tube.
Figure 4:
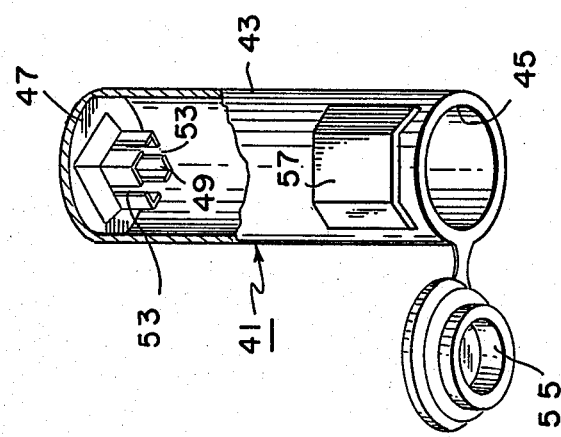
FIG. 4 is a perspective view partly broken away of a needle holder constructed according to the teachings of the present invention with the cover in the off position.

Referring now to FIG. 3, there is shown a section view of a typical blood collection tube 35, commonly referred to as a pilot tube. Pilot tube 35 is hollow, evacuated, made of glass, plastic or other similar material and is open at one end 37. A stopper 39 having a recess 39-1 and a base 39-2 made of rubber or other similar material is mounted in the open end 37 to seal tube 35 and maintain the vacuum therein.

Referring now to FIGS. 4 through 7 there is shown a holder constructed according to this invention and identified by reference numeral 41.

Holder 41, is a unitary structure and is made of a fairly sturdy plastic material such as polypropylene. Holder 41 is in the shape of an elongated tubular member 43 having a slightly tapered sidewall, first or bottom end 45 and a second or top end wall 47. The wall thickness of member 43 is about 0.030 inches. The internal cross-sectional diameter of tubular member 43 over its entire length is greater than the external cross-sectional diameter D2 of pilot tube 35 so that pilot tube 35 may be inserted therein from one end to the other. The length L1 of tubular member 43 is less than the length L2 of pilot tube 35 so that pilot tube 35 can be held from the bottom as it is inserted into holder 41 from bottom end 45 and pushed through toward top end 47. For example, if pilot tube 35 is four inches long, tubular member 43 may be about two and one quarter inches in length.

Bottom end 45 of tubular member 43 is open to allow insertion of pilot tube 35, the opening including a peripheral flange 45-1. Top end wall 47 of tubular member 43 has a rectangular bottom 49 which is sized and shaped so as to be about equal to the size and shape of hubs 25 and 30. Accordingly, when primary needle 21 (or in-line needle 27) is inserted into tubular member 43, the hub at the back end of the respective needle will frictionally engage and be snugly held within opening 49. Opening 49 has tapered sidewalls 50 to facilitate easy insertion of a needle and includes an extension or sleeve 51, rectangular in cross section which projects inward and has slots 53. Extension 51 serves to provide additional surface area for gripping hub 25 and maintaining primary needle 22 (or in-line needle 27) axially aligned within tubular member 43 while the slots 53 serve to increase the gripping action of the sidewalls of extension 51.

A cover 55 is hingedly attached to tubular member 43 for selectively closing off end 45 and a mounting bracket 57 is integrally formed on the outer wall of tubular member 43 for mounting the holder 41 on a holding bracket or hook or other similar device, when desired.

Figure 8:
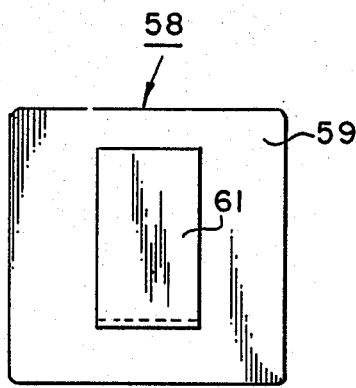
FIGS. 8 and 9 are front and side views, respectively, of a holding bracket for use with the needle holder shown in FIG. 4.
Figure 9:
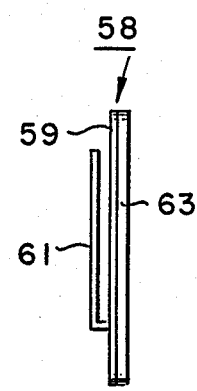

An example of such a holding bracket 58 for use with holder 41 is shown in FIGS. 8 and 9 and is identified by reference numeral 58. Holding bracket 58 includes a plate 59 having a hook 61 extending out from the front and an adhesive 63 on the back. Holding bracket 58 may be mounted by adhesive 63 on a bedframe or other structure.

Holder 41 may be used as a receptacle for temporary or permanent storage of primary needle 21 (or in-line needle 27) and/or as a device to assit a nurse or technician in inserting primary needle 21 (or in-line needle 27) into pilot tube 35.

Figure 10:
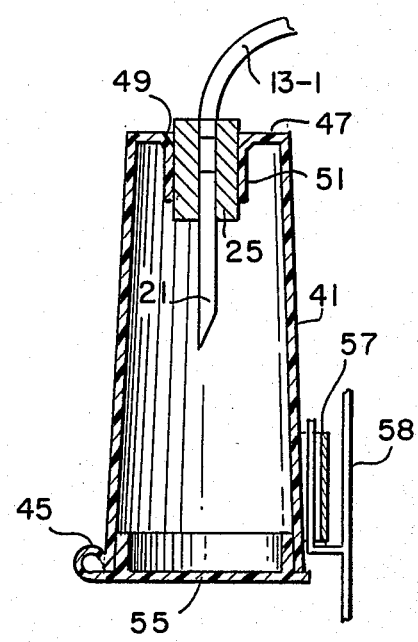
FIG. 10 is a section view showing the primary needle of the apparatus in FIG. 1 inserted into the device shown in FIG. 4 with the cover of the device being on and the device being mounted on the holding bracket shown in FIG. 8.

FIG. 10 shows the holder 41 in use as a receptacle. For this application holder 41 is mounted on bracket 58 and end 45 is closed by cover 55. Primary needle (or in-line needle 27) is inserted into end wall 47 so that hub 25 engages the inside wall of opening 49 and extension 51. Since end 45 is closed any blood which drips off of the tip of the needle will be contained within holder 41.

Figure 11:
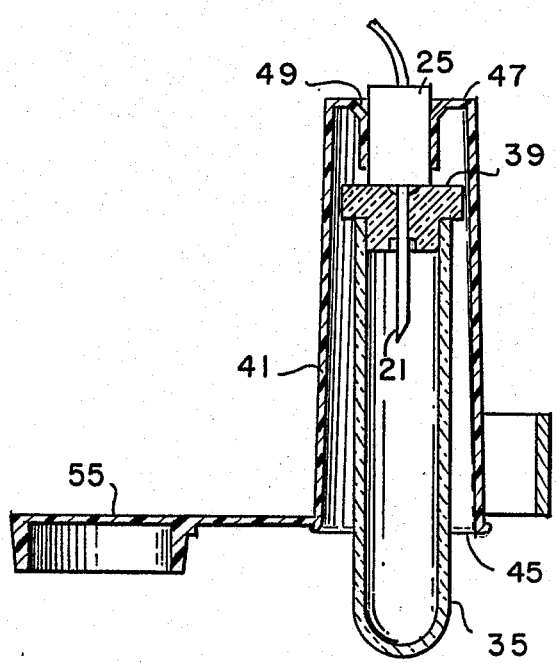
FIG. 11 is a section view showing the primary needle of the apparatus in FIG. 1 inserted into the device of the invention from one end and the tube in FIG. 3 inserted into the device from the other end, with the distal end of the needle extending through the stopper at the open end of the tube.

In using the device to assist in inserting primary needle 21 (or in-line needle 27) into pilot tube 35, holder 41 is inverted and the needle inserted up through end 47 so that hub 25 (or hub 30) engages opening 49. Cover 55 is removed and pilot tube 35 inserted through the open end 45 and pushed down until the tip of primary needle 21 penetrates through the stopper 39. This arrangement is shown in FIG. 11. As can be seen, penetration of primary needle 21 inside the pilot tube 35 is achieved inside of holder 41, thereby completely eliminating the possibility of the nurse or technician being stuck by the needle. Alternatively, the pilot tube 35 could be inserted into holder 41 first and the needle inserted after that.

As can be appreciated, holder 41 can be used with either primary needle 21 or in-line needle 27 since they both contain the same size and shaped hub.

Figure 12:
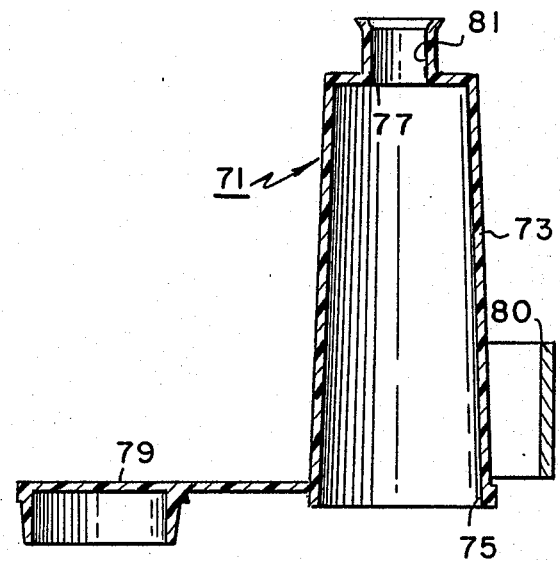
FIG. 12 is a section view of another embodiment of a device according to the present invention.
Figure 6:
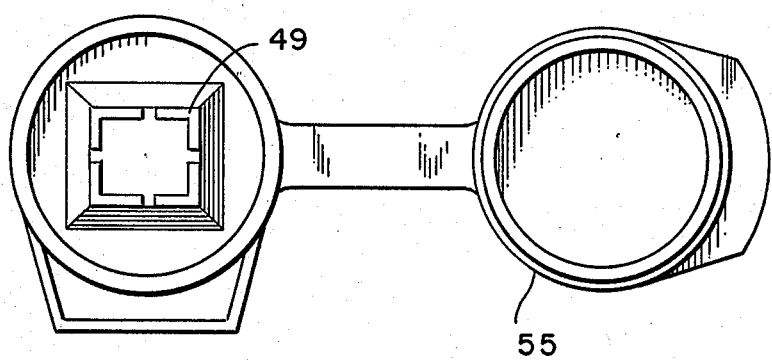
FIGS. 6 and 7 are top and bottom views, respectively, of the device shown in FIG. 4.
Figure 7:
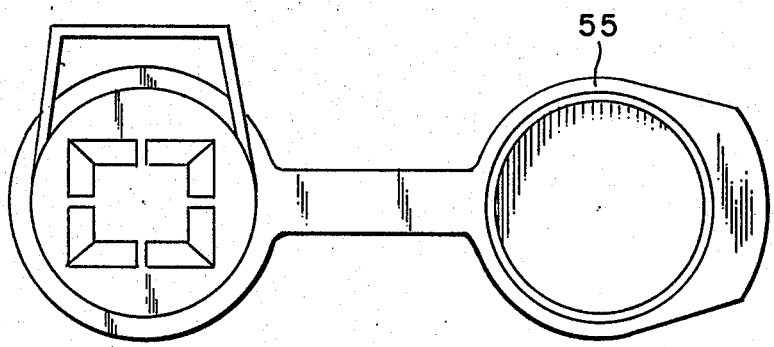

FIG. 12 shows another embodiment of the invention. The holder, identified by reference numeral 71, includes a tubular member 73 open at the bottom end 75 and having an appropriately sized opening 77 at the top end, a hingedly attached cover 79 and an integrally formed mounting bracket 80 all as in the first embodiment. Embodiment 71 also includes an extension 81; however, extension 81 projects outward rather than inward as with the corresponding extension 51 in the first embodiment.

The embodiments of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A holder for a surgical needle having a sharp proximal end and a hub portion at the distal end, comprising
   (a) a tubular member open at one end for receiving the stopper end of a blood collection pilot tube, the inner diameter of said tubular member being slightly greater than the outer diameter of said blood collection pilot tube and the length of said tubular member being greater than the length of the needle;
   (b) the other end of said tubular member including an integral end wall;
   (c) said end wall including an integral sleeve portion defining an enlarged opening in said end wall for receiving the sharp proximal end of the needle, the outer portion of said sleeve portion having an outwardly tapered sidewall, whereby said enlarged opening becomes progressively smaller in the direction of the interior of said tubular member to guide the needle proximal end therein, the configuration of said sleeve portion corresponding with the configuration of the needle hub portion, said sleeve portion containing slots for increasing the gripping action thereof, whereby when the needle is inserted into said tubular member through said opening, the needle hub is wedged within and held by said sleeve portion to arrest the further inserting of the needle, and when a stoppered blood collection pilot tube is inserted into the tubular member open end, the sharp proximal end of the needle penetrates the stopper of the blood collection pilot tube to deposit blood into the tube via the needle while preventing the sharp proximal end of the needle from contacting the user.

2. Apparatus as defined in claim 1, wherein said tubular member further includes an integral end cover for closing said open end, said end cover including a flexible hinge strap connected with said tubular member open end for movement between open and closed positions.

3. Apparatus as defined in claim 2, wherein said tubular member further includes an integral mounting bracket arranged on the outer surface thereof.

4. Apparatus as defined in claim 3, wherein said holder is formed of synthetic plastic material.

5. Apparatus as defined in claim 4, wherein said sleeve portion extends interiorly of said tubular member.

6. Apparatus as defined in claim 4, wherein said sleeve portion extends exteriorly of said tubular member.

* * * * *